United States Patent [19]

Fischer et al.

[11] 3,984,450

[45] Oct. 5, 1976

[54] THIOLCARBAMATES

[75] Inventors: Adolf Fischer, Mutterstadt; Ludwig Schuster, Limburgerhof; Wolfgang Rohr, Mannheim; Karl Eicken; Hans-Dieter Hoffmann, both of Ludwigshafen, all of Germany

[73] Assignee: BASF Aktiengesellschaft, Ludwigshafen am Rhine, Germany

[22] Filed: June 28, 1974

[21] Appl. No.: 484,143

[30] Foreign Application Priority Data

July 7, 1973 Germany............................ 2334601

[52] U.S. Cl............................... 260/455 A; 71/100
[51] Int. Cl.²....................................... C07C 155/03
[58] Field of Search................................. 260/455 A

[56] References Cited
UNITED STATES PATENTS 3,185,720  5/1965  Tilles et al. ...................... 260/455 A

FOREIGN PATENTS OR APPLICATIONS 882,110  11/1961  United Kingdom............. 260/455 A

*Primary Examiner*—Lewis Gotts
*Assistant Examiner*—D. R. Phillips
*Attorney, Agent, or Firm*—Johnston, Keil, Thompson & Shurtleff

[57] ABSTRACT

New and valuable thiolcarbamates having a good herbicidal action, herbicides containing these compounds, and a process for controlling the growth of unwanted plants with these compounds.

3 Claims, No Drawings

THIOLCARBAMATES

This application discloses and claims subject matter described in German patent application P 23 34 601.2, filed July 7, 1973, which is incorporated herein by reference.

The present invention relates to new and valuable thiolcarbamates, herbicides containing them, and the control of unwanted plant growth with these compounds.

It is known to use thiolcarbamates for controlling unwanted plants in crops such as barley, wheat and rice. However, these prior art thiolcarbamates have, when used preemergence, a fairly poor action on Panicum and Poa species and Digitaria sanguinalis, and a weak action in general when low application rates are employed. Their action is particularly poor when used postemergence. Furthermore, they have a fairly high vapor pressure and must therefore be incorporated into the soil.

We have now found that substituted N-cyclohexylthiocarbamates of the formula

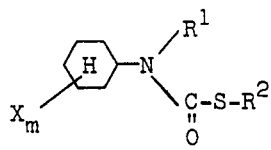

wherein $R^1$ denotes alkyl (methyl, ethyl, propyl, isopropyl, butyl, isobutyl, tert-butyl, sec-butyl), alkenyl (allyl, methallyl) or alkynyl (propargyl), butynyl), $R^2$ denotes an aliphatic radical (methyl, ethyl, propyl, isopropyl, butyl, sec-butyl, tert-butyl, isobutyl), unsubstituted benzyl or benzyl substituted by halogen, alkyl, nitro or alkoxy, X denotes methyl and/or ethyl and/or propyl and/or isopropyl, and $m$ denotes one of the integers 1 and 2, have, compared with the prior art compounds, better compatibility with crop plants, especially Beta vulgaris, and a better herbicidal action when used preemergence on Panicum, Poa and Digitaria species and when used postemergence on Echinochloa crus-galli, Lolium species, Avena fatua and Alopecurus myosuroides. The new compounds also have a lower vapor pressure.

The active ingredients may be prepared by reacting a thiol chloroformate with a substituted cyclohexylamine of the formula

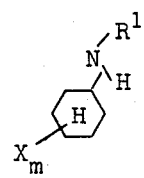

$R^1$, X and $m$ having the above meanings. The new active ingredients may also be obtained by allowing the substituted cyclohexylamines, in the form of their N-acyl halides, to react with mercaptans. The active ingredients are further accessible by reaction of substituted cyclohexylamine with carbonyl sulfide and subsequent alkylation of the salt of monothiocarbamic acid thus obtained.

The cyclohexylamines used as starting materials may be prepared by the following well-known methods:

a. by catalytic reduction of appropriately substituted anilines;
b. by N-alkylation of ring-substituted primary cyclohexylamines;
c. by catalytic, chemical or electrochemical reduction of substituted cyclohexane oximes followed by N-alkylation of the cyclohexylamines obtained.

Substituted cyclohexylamines obtained by either method *a* or *b* are preferred.

The following example demonstrates the preparation of the new active ingredients.

EXAMPLE

At room temperature and while stirring, a mixture of 16 parts by weight of N-ethyl-3-methylcyclohexylamine and 10.1 parts by weight of triethylamine is dripped into a mixture of 12.5 parts by weight of thioethyl chloroformate and 160 parts by weight of benzene. The mixture is subsequently boiled for 2 hours under reflux. The precipitate is removed and the benzene solution washed with water, dried with magnesium sulfate and concentrated in vacuo. Distillation of the residue gives S-ethyl-N-ethyl-N-3-methylcyclohexylthiolcarbamate boiling at 98° to 102° C (0.3 mm Hg).

The following compounds may be prepared analogously:

|  | b.p. | (mm Hg) |
|---|---|---|
| S-ethyl-N-ethyl-N-2-methylcyclohexyl-thiolcarbamate | 103°C | (0.01) |
| S-ethyl-N-ethyl-N-4-methylcyclohexyl thiolcarbamate | 102°C | (0.2) |
| S-propyl-N-ethyl-N-2-methylcyclohexyl-thiolcarbamate | 126–128°C | (0.2) |
| S-methyl-N-ethyl-N-2-methylcyclohexyl-thiolcarbamate | 98–100°C | (0.01) |
| S-isopropyl-N-ethyl-N-2-methylcyclohexyl-thiolcarbamate | 103–104°C | (0.01) |
| S-benzyl-N-ethyl-N-4-methylcyclohexyl-thiolcarbamate | 163–172°C | (0.3) |
| S-benzyl-N-ethyl-N-2-methylcyclohexyl-thiolcarbamate | 158–160°C | (0.1) |
| S-ethyl-N-isopropyl-N-4-ethylcyclohexyl-thiolcarbamate | 155°C | (2.0) |
| S-ethyl-N-isopropyl-N-2-ethylcyclohexyl-thiolcarbamate | 108°C | (0.3) |
| S-benzyl-N-isopropyl-N-4-ethylcyclohexyl-thiolcarbamate | 186–196°C | (0.5) |
| S-benzyl-N-isopropyl-N-2-methylcyclohexyl-thiolcarbamate | m.p. 62°C | |
| S-ethyl-N-isopropyl-N-4-isopropylcyclohexyl-thiolcarbamate | m.p. 58°C | |

-continued

| | b.p. | (mm Hg) |
|---|---|---|
| S-benzyl-N-isopropyl-N-4-isopropylcyclo-hexylthiolcarbamate | m.p. 52°C | |
| S-ethyl-N-butyl-N-3-methylcyclohexyl-thiolcarbamate | 126°C | (0.4) |
| S-methyl-N-butyl-N-3-methylcyclohexyl-thiolcarbamate | 133–134°C | (0.3) |
| S-isorpopyl-N-butyl-N-3-methylcyclohexyl-thiolcarbamate | 117–118°C | (0.05) |
| S-propyl-N-butyl-N-3-methylcyclohexyl-thiolcarbamate | 142–143°C | (0.1) |
| S-ethyl-N-butyl-N-2-methylcyclohexyl-thiolcarbamate | 112°C | (0.4) |
| S-benzyl-N-butyl-N-2-methylcyclohexyl-thiolcarbamate | 184–194°C | (0.4) |
| S-benzyl-N-butyl-N-3-methylcyclohexyl-thiolcarbamate | 175–176°C | (0.1) |
| S-ethyl-N-methyl-N-3,6-dimethylcyclo-hexylthiolcarbamate | 142°C | (2.0) |
| S-benzyl-N-methyl-N-3,6-dimethylcyclo-hexylthiolcarbamate | 189°C | (0.4) |
| S-ethyl-N-allyl-N-2-methylcyclohexyl-thiolcarbamate | 112–113°C | (0.2) |
| S-propyl-N-allyl-N-2-methylcyclohexyl-thiolcarbamate | 138–140°C | (0.4) |
| S-benzyl-N-allyl-N-2-methylcyclohexyl-thiolcarbamate | 178–180°C | (0.1) |
| S-ethyl-N-propargyl-N-2-methylcyclohexyl-thiolcarbamate | 125–127°C | (0.1) |
| S-benzyl-N-propargyl-N-2-methylcyclohexyl-thiolcarbamate | 186–187°C | (0.01) |
| S-4-chlorobenzyl-N-allyl-N-2-methylcyclo-hexylthiolcarbamate | 206°C | (0.25) |
| S-4-chlorobenzyl-N-propargyl-N-2-methylcyclo-hexylthiolcarbamate. | | |

The new active ingredients have a strong herbicidal action and may therefore be used as weedicides or for controlling the growth of unwanted plants. Whether the new active ingredients are used as total or selective agents depends in essence on the amount of ingredient used per unit area.

By "weeds" and "unwanted plant growth" are meant all monoco-yl-tyledonous and dicotyledonous plants which grow in loci where they are not desired.

The agents according to the invention may therefore be used for controlling for instance Graminae, such as
Cynodon spp.
Digitaria spp.
Echinochloa spp.
Setaria spp.
Panicum spp.
Alopecurus spp.
Lolium spp.
Sorghum spp.
Agropyron spp.
Phalaris spp.
Apera spp.
Dactylis spp.
Avena spp.
Bromus spp.
Uniola spp.
Poa spp.
Leptochloa spp.
Brachiaria spp.
Eleusine spp.
Cenchrus spp.
Eragrostis spp.
Etc.;
Cyperaceae, such as
Carex spp.
Cyperus spp.
Scirpus spp.
Eleocharis spp.
etc.;
dicotyledonous weeds, such as
Malvaceae, e.g.,
Abutilon theoprasti
Sida spp.
Malva spp.
Hibiscus spp.
etc.;
Compositae, such as
Ambrosia spp.
Lactuca spp.
Senecio spp.
Sonchus spp.
Xanthium spp.
Iva spp.
Galinsoga spp.
Taraxacum spp.
Chrysanthemum spp.
Cirisum spp.
Centaurea spp.
Tussilago spp.
Lapsana communis
Tagetes spp.
Erigeron spp.
Anthemis spp.
Matricaria spp.
Artemisia spp.
etc.;
Convolvulaceae, such as
Convolvulus spp.
Ipomoea spp.
Jaquemontia tamnifolia
Cruceferae, such as
Cuscuta spp.
etc.;

-continued

Barbara vulgaris
Brassica spp.
Capsella spp.
Sisymbrium spp.
Thlaspi spp.
Sinapis arvensis
Raphanus spp.
Arabidopsis thaliana
Descurainia spp.
Draba spp.
Coronopus didymus
Lepidium spp.
etc.;
Geraniaceae, such as
Erodium spp.
Geranium spp.
etc.;
Portulacaceae, such as
Portulaca spp.
etc.;
Primulaceae, such as
Anagallis arvensis
Lysimachia spp.
etc.;
Rubiaceae, such as
Richardia spp.
Galium spp.
Diodia spp.
etc.;
Scrophulariaceae, such as
Linaria spp.
Veronica spp.
Digitalis spp.
etc.;
Solanaceae, such as
Physalis spp.
Solanum spp.
Datura spp.
Nicandra spp.
etc.;
Urticaceae, such as
Urtica spp.
etc.;
Violaceae, such as
Viola spp.
etc.;
Zygophyllaceae, such as
Tribulus terrestis
etc.;
Euphorbiaceae, such as
Mercurialis annua
Euphorbia spp.
Umbelliferae, such as
Daucus carota
Aethusa cynapium
Ammi majus
etc.;
Commelinaeae, such as
Commelina spp.
etc.;
Labiatae, such as
Lamium spp.
Galeopsis spp.
etc.;
Leguminosae, such as
Medicago spp.
Trifolium spp.
Vicia spp.
Lathyrus spp.
Sesbania exaltata
Cassia spp.
etc.;
Plantaginaceae, such as
Plantago spp.
etc.;
Polygonaceae, such as
Polygonum spp.
Rumex spp.
Fagopyrum spp.
etc.;
Aizoaceae, such as -continued

| | |
|---|---|
| *Mollugo verticillata* | etc.; |
| *Amaranthaceae*, such as | |
| *Amaranthus* spp. | etc.; |
| *Boraginaceae*, such as | |
| *Amsinckia* spp. | *Anchusa* spp. |
| *Myostis* spp. | etc.; |
| *Lithospermum* spp. | |
| *Caryophyllaceae*, such as | |
| *Stellaria* spp. | *Silene* spp. |
| *Spergula* spp. | *Cerastium* spp. |
| *Saponaria* spp. | *Agrostemma githago* |
| *Scleranthus annuus* | etc.; |
| *Chenopodiaceae*, such as | |
| *Chenopodium* spp. | *Atriplex* spp. |
| *Kochia* spp. | *Monolepsis nuttaliana* |
| *Salsola kali* | etc.; |
| *Lynthraceae*, such as | |
| *Cuphea* spp. | etc.; |
| *Oxalidaceae*, such as | |
| *Oxalis* spp. | etc. |
| *Ranunculaceae*, such as | |
| *Ranunculus* spp. | *Adonis* spp. |
| *Delphinium* spp. | etc.; |
| *Papaveraceae*, such as | |
| *Papaver* spp. | etc.; |
| *Fumaria officinalis* | |
| *Onagraceae*, such as | |
| *Jussiaea* spp. | etc.; |
| *Rosaceae*, such as | |
| *Alchemillia* spp. | etc.; |
| *Potentilla* spp. | |
| *Potamogetonaceae*, such as | |
| *Potamogeton* spp. | etc.; |
| *Najadaceae*, such as | |
| *Najas* spp. | etc.; |
| *Marsileaceae*, such as | |
| *Marsilea quadrifolia* | etc. |

The amount used of the agents of the invention may vary and depends on the effect desired; it generally is from 0.1 to 15 or more, and preferably from 0.2 to 6, kg per hectare.

The new agents may be employed in cereal crops, such as

| | |
|---|---|
| *Avena* spp. | *Sorghum* |
| *Triticum* spp. | *Zea mays* |
| *Hordeum* spp. | *Panicum miliaceum* |
| *Secale* spp. | *Oryza* spp. |
| and in dicotyledon crops, such as | |
| *Cruciferae*, e.g. | |
| *Brassica* spp. | *Raphanus* spp. |
| *Sinapis* spp. | *Lepidium* spp. |
| *Compositae*, e.g. | |
| *Lactua* spp. | *Carthamus* spp. |
| *Helianthus* spp. | *Scorzonera* spp. |
| *Malvaceae*, e.g. | |
| *Gossypium hirsutum* | |
| *Leguminosae*, e.g. | |
| *Medicago* spp. | *Phaseolus* spp. |
| *Trifolium* spp. | *Arachis* spp. |
| *Pisum* spp. | *Glycine max.* |
| *Chenopodiaceae*, e.g. | |
| *Beta vulgaris* | |
| *Spinacia* spp. | |
| *Solanaceae*, e.g. | |
| *Solanum* spp. | *Capsicum annuum* |
| *Nicotiania* spp. | |
| *Linaceae*, e.g. | |
| *Linum* spp. | |
| *Umbelliferae*, e.g. | |
| *Petroselinum* spp. | *Apium graveolens* |
| *Daucus carota* | |
| *Rosaceae*, e.g. | |
| *Gragaria* | |
| *Cucurbitaceae*, e.g. | |
| *Cucumis* spp. | *Cucurbita* spp. |
| *Liliaceae*, e.g. | |
| *Allium* spp. | |
| *Vitaceae*, e.g. | |
| *Vitis vinifera* | |
| *Bromeliaceae*, e.g. | |
| *Ananas sativus*. | |

Application may be effected for instance in the form of directly sprayable solutions, powders, suspensions, dispersions, emulsions, oil dispersions, pastes, dusts or granules. The forms of application depend entirely on the purpose for which the agents are being used; in any case they should ensure a fine distribution of the active ingredient.

For the preparation of solutions, emulsions, pastes and oil dispersions to be sprayed direct, mineral oil fractions of medium to high boiling point, such as kerosene or diesel oil, further coal-tar oils and oils of vegetable or mineral origin, aliphatic, cyclic and aromatic hydrocarbons such as benzene, toluene, xylene, paraffin, tetrahydronaphthalene, alkylated naphthalenes, methanol, ethanol, propanol, butanol, chloroform, carbon tetrachloride, cyclohexanol, cyclohexanone, chlorobenzene, isophorone, etc., and strongly polar solvents such as dimethyl-formamide and dimethyl sulfoxide are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agents, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfonated hexadecanols, heptadecanols, and octadecanols, salts of sulfonated fatty alcohol glycol ether, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. The particle size is for example 0.01 to 5 mm. Examples of solid carriers are mineral earths such as silica gel, silicic acid, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, preferably from 0.5 to 90% by weight of active ingredient.

There may be added to the compositions or individual active ingredients (if desired, immediately before and/or after the active ingredients of the invention) oils of various types, herbicides, fungicides, nematocides, insecticides, bactericides, trace elements, fertilizers, antifoams (e.g., silicones), growth regulators, antidotes and other herbicidally effective compounds as substituted anilines,
substituted aryloxycarboxylic acids and salts, esters and amides thereof,
substituted ethers,
substituted arsonic acids and their salts, esters and amides,
substituted benzimidazoles,
substituted benzisothiazoles,
substituted benzothiadiazinone dioxides,
substituted benzoxazines,
substituted benzoxazinones,
substituted benzothiadiazoles,
substituted biurets,
substituted quinolines,
substituted carbamates,
substituted aliphatic carboxylic acids and their salts, esters and amides,
substituted aromatic carboxylic acids and their salts, esters and amides,
substituted carbamoylalkylthio- or -dithiophosphates,
substituted quinazolines,
substituted cycloalkylamidocarbothiolic acids, and their salts, esters and amides,
substituted cycloalkylcarbonamidothiazoles,
substituted dicarboxylic acids and their salts, esters and amides,
substituted dihydrobenzofuranyl sulfonates,
substituted disulfides,
substituted dipyridylium salts,
substituted dithiocarbamates,
substituted dithiophosphoric acids and their salts, esters and amides,
substituted ureas,
substituted hexahydro-1-H carbothiolates,
substituted hydantoins,
substituted hydrazides,
substituted hydrazonium salts,
substituted isooxazole pyrimidones,
substituted imidazoles,
substituted isothiazole pyrimidones,
substituted ketones,
substituted naphthoquinones,
substituted aliphatic nitriles,
substituted aromatic nitriles,
substituted oxadiazoles,
substituted oxadiazinones,
substituted oxadiazolidine diones,
substituted oxadiazine diones, substituted phenols and their salts and esters,
substituted phosphonic acids and their salts, esters and amides,
substituted phosphonium chlorides,
substituted phosphonalkylglycines,
substituted phosphites,
substituted phosphoric acids and their salts, esters and amides,
substituted piperidines,
substituted pyrazoles,
substituted pyrazole alkylcarboxylic acids and their salts, esters and amides,
substituted pyrazolium salts,
substituted pyrazolium alkyl sulfates,
substituted pyridazines,
substituted pyridazones,
substituted pyridine carboxylic acids and their salts, esters and amides,
substituted pyridines,
substituted pyridine carboxylates,
substituted pyridinones,
substituted pyrimidines,
substituted pyrimidones,
substituted pyrrolidine carboxylic acid and its salts, esters and amides,
substituted pyrrolidines,
substituted pyrrolidones,
substituted arylsulfonic acids and their salts, esters and amides,
substituted styrenes,
substituted tetrahydrooxadiazine diones,
substituted tetrahydrooxadiazole diones,
substituted tetrahydromethanoindes,
substituted tetrahydrooxadiazole thiones,
substituted tetrahydrodiazine thiones,
substituted tetrahydrothiadiazole diones,
substituted aromatic thiocarbonylamides,
substituted thiocarboxylic acids and their salts, esters and amides,
substituted thiol carbamates,
substituted thioureas,
substituted thiophoshoric acids and their salts, esters and amides,
substituted triazines,
substituted uracils,
substituted uretidine diones.

These agents may be added to the herbicides according to the invention in a ratio by weight of from 1 : 10 to 10 : 1. The same applies to oils, fungicides, nematocides, insecticides, bactericides, trace elements, fertilizers, antidotes and growth regulators.

The agents according to the invention may be applied either once or several times before or after planting, before sowing, pre- or postemergence, or during emergence of the crop plants of weeds.

EXAMPLE 2

In the greenhouse, loamy sandy soil was filled into pots and sown with the seeds of various plants. The soil prepared in this manner was then immediately treated with 2.5 kg per hectare of S-ethyl-N-ethyl-N-2-methyl-cyclohexylthiolcarbamate (I) and 2.5 kg per hectare of the comparative agent S-ethyl-N-ethyl-N-cyclohexyl-thiolcarbamate (II), each compound being dispersed or emulsified in 500 liters of water per hecrare.

After 3 to 4 weeks it was ascertained that I had better crop plant compatibility than II, combined with a superior herbicidal action.

The results are given below:

| Active ingredient kg/ha | I 2.5 | II 2.5 |
|---|---|---|
| Crop plants: | | |
| Beta vulgaris | 0 | 10 |
| Spinacia oleracea | 0 | 5 |
| Unwanted plants: | | |
| Avena fatua | 92 | 82 |
| Echinochloa crus-galli | 85 | 80 |
| Lolium multiflorum | 90 | 86 |
| Lolium perenne | 90 | 86 |
| Alopecurus myosuroides | 90 | 85 |

-continued

| Active ingredient kg/ha | I 2.5 | II 2.5 |
|---|---|---|
| Apera spica venti | 100 | 87 |
| Bromus tectorum | 85 | 76 |
| Bromus secalinus | 85 | 75 |
| Setaria glauca | 90 | 80 |
| Panicum capillare | 100 | 82 |
| Digitaria sanguinalis | 95 | 80 |
| Poa annua | 100 | 85 |
| Poa trivialis | 100 | 85 |
| Festuca rubra | 100 | 100 |

0 = no damage
100 = complete destruction

EXAMPLE 3

In the greenhouse, various plants were trated at a growth height of from 3 to 11 cm with 3 kg per hectare of I and of II, each compound being dispersed or emulsified in 500 liters of water per hectare.

After 2 to 3 weeks it was ascertained that I had better crop plant compatibility than II, combined with a superior herbicidal action.

The results are given below:

| Active ingredient kg/ha | I 3.0 | II 3.0 |
|---|---|---|
| Crop plants: | | |
| Beta vulgaris | 8 | 15 |
| Spinacia oleracea | 3 | 8 |
| Unwanted plants: | | |
| Avena fatua | 65 | 35 |
| Echinochloa crus-galli | 80 | 45 |
| Lolium multiflorum | 90 | 67 |
| Alopecurus myosuroides | 85 | 43 |

0 = no damage
100 = complete destruction

EXAMPLE 4

In the greenhouse, loamy sandy soil was filled into pots and sown with the seeds of various plants. The soil prepared in this manner was then immediately treated with 0.5 kg per hectare of I and of II, each compound being emulsified or dispersed in 500 liters of water per hectare.

After 3 to 4 weeks it was ascertained that I had a better herbicidal action than II, combined with the same good crop plant compatibility.

The results are given below:

| Active ingredient kg/ha | I 0.5 | II 0.5 |
|---|---|---|
| Crop plants: | | |
| Beta vulgaris | 0 | 0 |
| Spinacia oleracea | 0 | 0 |
| Unwanted plants: | | |
| Avena fatua | 100 | 12 |
| Echinochloa crus-galli | 100 | 20 |
| Poa annua | 90 | 15 |
| Lolium multiflorum | 95 | 22 |
| Sinapis arvensis | 65 | 2 |

0 = no damage
100 = complete destruction

The action of the following compounds corresponds to that of I in Examples 2, 3 and 4:
  ethyl N-ethyl-N-m-methylcyclohexylthiolcarbamate;
  benzyl N-ethyl-N-o-methylcyclohexylthiolcarbamate;
  ethyl N-ethyl-N-p-methylcyclohexylthiolcarbamate;

EXAMPLE 5

90 parts by weight of the compound of Example 1 is mixed with 10 parts by weight of N-methyl-α-pyrrolidone. A mixture is obtained which is suitable for application in the form of very fine drops.

EXAMPLE 6

20 parts by weight of compound I from Example 2 is dissolved in a mixture consisting of 80 parts by weight of xylene, 10 parts by weight of the adduct of 8 to 10 moles of ethylene oxide to 1 mole of oleic acid-N-monoethanolamide, 5 parts by weight of the calcium salt of dodecylbenzenesulfonic acid, and 5 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 7

20 parts by weight of compound I is dissolved in a mixture consisting of 40 parts by weight of cyclohexanone, 30 parts by weight of isobutanol, 20 parts by weight of the adduct of 7 moles of ethylene oxide to 1 mole of isooctylphenol, and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 8

20 parts by weight of compound I is dissolved in a mixture consisting of 25 parts by weight of cyclohexanol, 65 parts by weight of a mineral oil fraction having a boiling point between 210° and 280° C, and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 9

20 parts by weight of compound I is well mixed with 3 parts by weight of the sodium salt of diisobutylnaphthalene-α-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquid is obtained containing 0.1% by weight of the active ingredient.

EXAMPLE 10

3 parts by weight of compound I is intimately mixed with 97 parts by weight of particulate kaolin. A dust is obtained containing 3% by weight of the active ingredient.

EXAMPLE 11

30 parts by weight of compound I is intimately mixed with a mixture consisting of 92 parts by weight of powdered silica gel and 8 parts by weight of paraffin oil which has been sprayed onto the surface of this silica gel. A formulation of the active ingredient is obtained having good adherence.

We claim:
1. A substituted N-cyclohexylthiolcarbamate of the formula
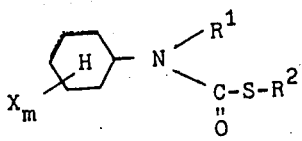
where $R^1$ is lower alkyl, allyl, methallyl or butynyl, $R^2$ is lower alkyl, benzyl or chlorobenzyl, X denotes methyl, and m denotes one of the integers 1 and 2.
2. S-ethyl-N-ethyl-N-2-methylcyclohexylthiolcarbamate.
3. S-ethyl-N-ethyl-N-3-methylcyclohexylthiolcarbamate.
* * * * *